United States Patent [19]

Brooker et al.

[11] Patent Number: 4,797,318

[45] Date of Patent: Jan. 10, 1989

[54] ACTIVE PARTICLE-CONTAINING NONWOVEN MATERIAL, METHOD OF FORMATION THEREOF, AND USES THEREOF

[75] Inventors: Ronald W. Brooker, Atlanta; Bernard Cohen, Duluth; David M. Jackson, Roswell, all of Ga.

[73] Assignee: Kimberly-Clark Corporation, Neenah, Wis.

[21] Appl. No.: 892,529

[22] Filed: Jul. 31, 1986

[51] Int. Cl.$^4$ .............................................. D04H 1/58
[52] U.S. Cl. .................................. 428/283; 428/286; 428/288; 428/296; 428/903
[58] Field of Search ............... 428/283, 286, 296, 905, 428/288, 903

[56] References Cited

U.S. PATENT DOCUMENTS

| | | | |
|---|---|---|---|
| 2,188,428 | 1/1940 | Evans | 183/51 |
| 2,272,394 | 2/1942 | Armstrong | 183/51 |
| 2,988,469 | 6/1961 | Watson | 154/101 |
| 3,274,758 | 9/1966 | Parman | 55/279 |
| 3,371,984 | 3/1968 | Kelly et al. | 21/53 |
| 3,801,400 | 4/1974 | Vogt | 156/167 |
| 3,971,373 | 7/1976 | Braun | 128/146.2 |
| 4,007,311 | 2/1977 | Harlan et al. | 428/286 |
| 4,041,203 | 8/1977 | Brock et al. | 428/157 |
| 4,217,386 | 8/1980 | Arons et al. | 428/198 |
| 4,257,791 | 3/1981 | Wald | 55/291 |
| 4,296,166 | 10/1981 | Ogino | 428/283 |
| 4,315,877 | 2/1982 | Coplan et al. | 264/45.9 |
| 4,342,811 | 8/1982 | Lopatin et al. | 428/220 |
| 4,429,001 | 1/1984 | Koplin | 428/283 |
| 4,433,024 | 2/1984 | Elan | 428/190 |
| 4,436,780 | 3/1984 | Hotchkiss et al. | 428/198 |
| 4,469,734 | 9/1984 | Minto et al. | 428/134 |
| 4,526,733 | 7/1985 | Lau | 264/12 |
| 4,663,220 | 5/1987 | Wisneski et al. | 428/221 |

FOREIGN PATENT DOCUMENTS

| | | |
|---|---|---|
| 156649 | 10/1985 | European Pat. Off. . |
| 0156160 | 10/1985 | European Pat. Off. . |
| 2151272 | 7/1985 | United Kingdom . |

*Primary Examiner*—Marion C. McCamish
*Attorney, Agent, or Firm*—Joseph P. Harps

[57] ABSTRACT

Particle-laden meltblown material, methods for forming such material, composite laminate fabrics using such material as a layer of the laminate, and uses of such material and/or laminate thereof are disclosed. The particle-laden meltblown material is a coform of the particles and meltblown fibers, consolidated into a meltblown material. The meltblown fibers are made of polymeric materials such that the fibers are tacky after extrusion from the meltblowing die and prior to consolidation as meltblown material; active particles (such as active carbon) are incorporated in the stream of meltblown fibers, as the fibers pass from the die to the consolidation surface, at a location where the fibers are tacky, so that the particles adhere to the surface of the fibers. The polymeric materials forming the meltblown fibers can be elastomeric materials, and/or blends of polymers. The formed meltblown material can be used as a layer of a laminate, with other layers of the laminate providing abrasion resistance and mechanical strength. The meltblown material, and/or laminate including the meltblown material, can be used for gas/vapor filtering and/or adsorbing, and specifically can be used for disposable vacuum cleaner bags and the like.

13 Claims, 1 Drawing Sheet

ACTIVE PARTICLE-CONTAINING NONWOVEN MATERIAL, METHOD OF FORMATION THEREOF, AND USES THEREOF

BACKGROUND OF THE INVENTION

The present invention relates to nonwoven material (e.g., webs), and laminates including such nonwoven material, wherein the nonwoven material is, e.g., a particle-meltblown web coform structure having particulate material incorporated in the meltblown web (e.g., uniformly and homogeneously distributed therethrough).

Moreover, the present invention relates to methods of forming such nonwoven material, e.g., by particle-meltblown web coforming techniques, and methods of forming laminates including such nonwoven material, as well as uses for such nonwoven material and laminates.

It has been desired to provide porous particle-laden nonwoven material (such as webs), e.g., for filtering purposes, wherein the particles are loaded to a maximum amount in the web, the particles being held in the web without the web suffering from a "dusting" problem (that is, without the particles undesirably dropping out of the web). Moreover, it has been desired to provide such particle-laden webs as part of, e.g., a laminate, having various uses such as filtering uses.

U.S. Pat. No. 3,971,373 to Braun discloses a porous sheet product of a supported three-dimensional arrangement of particles, comprising a web of meltblown microfibers and the particles, no additional binder being necessary. This patent discloses that the particles are intermixed into a gaseous stream carrying the microfibers and become intermixed with the microfibers, the mixing occurring at a location spaced from the meltblowing die where the microfibers have become nontacky. The mixture is then collected on a collection screen, with the microfibers forming a web and the particles becoming dispersed in the web. The patent specifically discloses that the microfibers, mixed with the particles while the microfibers are not tacky, have no more than point contact with the particles, the particles usually being large enough to be physically entrapped within the interstices of the web. This patent further discloses that various polymers known to be useful in meltblowing, such as polypropylene, polyethylene, polyamides, and other polymers, can be used for forming the microfibers.

U.S. Pat. No. 4,433,024 to Eian discloses nonwoven sheet material laminates, including a permeable support fabric and, attached to the support fabric, a fibrous web including meltblown organic polymeric fibers and vapor-sorptive particles uniformly dispersed in the mass of fibers. This patent discloses that the support fabric can be either woven or nonwoven fabric, and can be laminated to both sides of the meltblown web to provide protection for the web and also to assure that particles are retained within the sheet material. This patent discloses that various means, such as adhesive bonding or attachment by sewing or ultrasonic welding, can be used to adhere the fabric to the sheet material. This patent also discloses that the particles can be mixed with the meltblown fibers under conditions that will produce an area contact with the particles, or, preferably, the particles are introduced into the stream of meltblown fibers at a point where the fibers have solidified sufficiently that the fibers will form only a point contact with the particles, as in the previously discussed U.S. Pat. No. 3,971,373.

U.S. Pat. No. 4,469,734 to Minto, et al. discloses formation of particle-laden web material, by incorporating absorbent particles into a stream of meltblown fibers while the fibers are still tacky, so that the particles are firmly attached to the fibers when the fibers set, a web being consolidated from the set fibers and particles. U.S. Pat. No. 2,988,469 to Watson discloses incorporation of particulate material in a stream of fibers while the fibers are still tacky (with no disclosure that the fibers are formed by meltblowing), the fibers being collected while still tacky, or afterwards, and formed into a web or sheet.

However, it is still desired to provide nonwoven meltblown webs having particles dispersed therethrough, wherein any problems with dusting are overcome, which webs can be formed easily using conventional meltblowing equipment.

SUMMARY OF THE INVENTION

Accordingly, it is an object of the present invention to provide nonwoven meltblown material (e.g., webs), particularly porous meltblown material, of various polymers, capable of holding particles distributed therein by coforming techniques without such particles dropping out therefrom, and methods of forming such material.

It is a further object of the present invention to provide nonwoven meltblown material, particularly porous meltblown material, having particles distributed throughout the material (e.g., uniformly and homogeneously distributed throughout the material), wherein problems of particles dropping out of the webs (e.g., dusting problems) are avoided, even at high particle loading in the material, and methods of forming such material.

It is a further object of the present invention to provide nonwoven meltblown material having particles distributed therethrough, wherein the particles are held in the meltblown material by more than mechanical entanglement, but wherein adhesives for the sole purpose of bonding the particles within the web need not be added.

It is a further object of the present invention to provide nonwoven meltblown material formed of meltblown fibers (e.g., microfibers) of thermoplastic polymeric materials, having particles dispersed throughout the meltblown material, wherein the meltblown fibers are made of elastomeric material, to thereby provide elastomeric meltblown material having particles distributed throughout the material.

It is a further object of the present invention to provide a composite laminate including meltblown material (e.g., at least one meltblown web) having particles distributed throughout the material, and a method of forming such laminate.

It is a further object of the present invention to provide a meltblown material (e.g., web) having particles distributed throughout the material, and/or a laminate including such meltblown material, having use as a filtering medium, e.g., for gases, and to provide various applications for such filtering medium.

It is a further object of the present invention to provide a porous meltblown material having particles dispersed therethrough, and/or a composite laminate including such meltblown material, with the particles being formed of an active substance which in use performs some desired reaction to a stimulus, such as absorbing components for the air or delivering substances to environmental air.

The present invention achieves each of the above objects by various techniques as described below, but each technique uses adhesive polymers for forming the meltblown fibers used in forming the meltblown material, and incorporate particles of desired substances into a stream of the meltblown fibers after formation of the fibers and while such fibers are still tacky. By incorporating the particles into the stream of meltblown fibers made of adhesive polymers, at a point where the fibers are still tacky, and then depositing the fibers and particulate material on a collecting surface as conventionally done in forming meltblown webs, a nonwoven meltblown material is provided wherein the particles are held on (adhere to) the surfaces of the fibers, and any dusting from the formed meltblown material, having particles distributed therethrough, can be minimized.

Moreover, by forming a composite laminate using such meltblown material as a layer of such composite laminate, together with at least one layer of sheet material, such as spunbond sheet material, having greater mechanical strength and abrasion resistance than the meltblown material, mechanical strength and abrasion resistance for the meltblown material are provided. In particular, by sandwiching the meltblown material with the layers of sheet material, a composite laminate with mechanical strength and abrasion resistance is provided. By using a porous sheet material, such as a porous spunbond sheet material, porosity of the meltblown material can be maintained while mechanical strength and abrasion resistance are achieved.

Moreover, as a further aspect of the present invention, a method of forming the particulate-laden meltblown material is provided. Specifically, the polymer is formed into meltblown fibers by conventional means, as discussed in U.S. Pat. No. 4,526,733 to Lau, assigned to the assignee of the present invention, the contents of which are incorporated by reference. The polymer used for forming the meltblown fibers is, at least in part, an adhesive polymer which can be formed into meltblown fibers by conventional meltblowing techniques. After the meltblown fibers are formed, and while the fibers are still tacky, and prior to collecting the fibers on a collecting surface, the particles are incorporated into the stream of meltblown fibers so as to adhere to the surface of the fibers, whereby upon collecting the fibers on a collecting surface and bonding the fibers to each other, a nonwoven meltblown web is formed having the particles dispersed and held throughout the web (e.g., uniformly and homogeneously distributed throughout the web).

Moreover, the present invention also provides a method of forming a composite laminate using such meltblown material as a layer of such laminate, e.g., as an intermediate web of such composite, with sandwiching webs of sheet material. For example, a laminate of a spunbond sheet/meltblown web/spunbond sheet can be formed by conventional techniques generally known for forming such laminate, with the specific technique discussed above, for forming the nonwoven meltblown web having particles distributed therethrough, being used to form the intermediate web of the laminate. With regard to a method of, generally, forming a laminate of spunbond sheet/meltblown web/spunbond sheet, attention is directed to U.S. Pat. No. 4,041,203 to Brock, et al., and U.S. Pat. No. 4,436,780 to Hotchkiss, et al., each assigned to the assignee of the present invention, the contents of each of which are incorporated by reference.

Moreover, the present invention provides various uses for the above-described nonwoven meltblown material having particles dispersed therethrough, and the above-described composite laminate, including use as a disposable vacuum cleaner bag; and, generally, in filtration products, both industrially and in the home, in uniforms for military applications, and in hazardous material handling and cleanup.

DETAILED DESCRIPTION OF THE INVENTION

Figure 1:
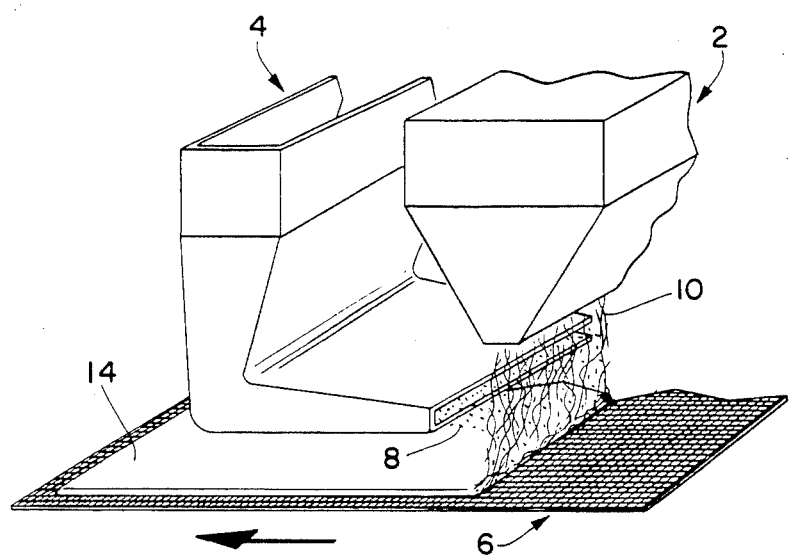
FIG. 1 is a perspective view of apparatus for forming the stream of meltblown fibers and for incorporating the particles into the stream, prior to collection of the fibers and particles into a meltblown web.

While the invention will be described in connection with specific and preferred embodiments, it will be understood that it is not intended to limit the invention to those embodiments. On the contrary, it is intended to cover all alterations, modifications and equivalents as may be included within the spirit and scope of the invention as defined by the appended claims.

The present invention in all of its aspects contemplates a meltblown material (e.g., web) of a polymeric material comprising at least in part an adhesive polymer, having particulate material dispersed through the meltblown material. By adhesive polymer is meant a polymeric material that can be meltblown to form fibers that are tacky in at least a zone where the particles are initially incorporated into the meltblown fiber stream, so that the particles adhere to the fibers. Generally, any polymer that is sufficiently tacky, between the die tip of the meltblowing apparatus and the collecting surface, to hold onto the particles that contact it, can be used as the polymeric material for the meltblown fibers, and thereby qualifies as adhesive polymers. In reality, this includes most polymers that are capable of being meltblown. Of course, different polymers have differing value as adhesive polymers. Any blend of adhesive polymers, or blend of adhesive polymers and other polymers, can also be used, as long as the two (or more) polymers forming the blend can be processed in the same range of conditions and they form a homogeneous melt. Moreover, the polymeric material for forming the meltblown fibers can be elastic, whereby particle-laden elastic meltblown material is formed.

Examples of such polymeric materials which can be utilized for forming the meltblown fibers, in forming the meltblown material, include blends of polyolefin polymers and adhesive polymers, such as blends of e.g., polypropylene polymer, together with polybutylene and/or polyethylene acrylic acid, both of which are tacky polymers. As an example, the blend can include polypropylene containing polybutylene and/or polyethylene acrylic acid as additional polymers, coextruded with the polypropylene in the meltblowing procedure, with amounts of the additional polymers being, for example, from 5-30% by weight of the total blend. Such blend, gives a tacky fiber which holds the particles much better than conventional polypropylene-only systems.

Generally, any polyolefin can be used as an adhesive polymer to provide the meltblown fibers of the present invention, as long as the polyolefin can be meltblown and is tacky in a zone where particulate material can be passed through the stream of meltblown fibers. For example, polybutylene (by itself), and similar polyolefins, can desirably be used to form the meltblown fibers.

Moreover, and as indicated previously, the polymeric materials used for forming the meltblown material can be elastomers so as to form, e.g., elastomeric meltblown webs having the particulate material dispersed therethrough. For example, polyurethane elastomeric materials, such as Estane ® 58887 Polyurethane (a thermoplastic polyester and polyether urethane elastomer, of B.F. Goodrich Chemical Co.); and A-B-A block copolymers, where A is a thermoplastic polymer and B is poly(ethylene-butylene), such as Kraton ®G 1657 (an A-B-A block copolymer, where A is polystyrene and B is poly(ethylene-butylene), of Shell Chemical Co.) can be used as the polymeric material, by itself or as part of a blend, for forming the meltblown fibers.

The meltblown material is, e.g., a sheet of entangled fibers that are held together by adhesion at contact points where one or more individual fibers meet. The adhesion at contact points is the result of the fibers being in contact while molten and remaining in contact when the polymer cools and hardens. The web is composed of fibers ranging in diameter from less than 1 micron, to 25 microns.

The particulate material, e.g., active material, incorporated in and co-formed with the meltblown material, can be selected from a wide variety of materials, depending on use of the web. For example, it is contemplated to use the meltblown material of the present invention as gas (or vapor) absorbent and/or gas (or vapor) filtering materials. Various particulates, such as activated carbon, potassium permanganate and baking soda, among others, can be incorporated in the meltblown web in particule form for gas absorbent or filtering purposes. Other materials, including deodorizing materials such as clays, diatomaceous earth, and complexes of potassium permanganate with active alumina can be used in particle form, incorporated in the meltblown material.

As for specific uses for particulates of different materials, the activated carbon-containing web can be used to scavenge air, and the baking soda-containing web can be used to remove odoriferous organics from the air. As can be appreciated, the presently listed particulate materials, and uses, are not limiting, but are merely exemplary of the materials which can be used. As for other particulates which can be incorporated in the meltblown web, see the previously discussed U.S. Pat. No. 3,971,373, such particulate materials as discussed therein being incorporated herein by reference.

The meltblown material of the present invention, having the particulate material distributed through the, e.g., meltblown web, provides particle loadings of, for example, up to 60% by weight of the total weight of the finished material (e.g., 40% to 60% by weight of the total weight of the finished material). By finished material is meant the material of the final product, e.g., the total laminate material if a laminate is being formed. By the present invention, dusting can be minimized at particle loadings of 60% by weight, and eliminated at 35% by weight. The particle size of the particulate material incorporated in the meltblown material plays an important role in the processility in forming the particle-laden meltblown web; the optimum particle size range is 50-150 microns.

As illustrative for feeding the particulate material into the stream of meltblown fibers, conventional particle feed apparatus, e.g., conventional particle spray apparatus, can be used. For example, conventional Oxy-dry ® (Oxy-Dry Corp.) or Gema ® electrostatic particle spray apparatus could be used.

The Oxy-dry ® powder feed system consists of three main parts: a feed hopper, a knurled roll, and an air stream. The particulate material (e.g., powder) is poured into the feed hopper, which sits on top of the knurled roll. The roll speed (rpm) is controlled by a rheostat and this acts as the control for the amount of powder fed into the air stream below the roll. The air stream then carries the powder into the stream of meltblown fibers. The main controls on the Oxy-dry ® system are the speed of the feedroll and the air velocity or quantity. The effective range of the feedroll speed (rpm) is 30%-100% of the maximum speed.

The particles can impact the stream of fibers anywhere between the die tip of the meltblowing apparatus and the fiber collecting surface, providing that the fibers are still tacky at the point of contact. Thus, depending on the polymer, as well as the meltblowing processing conditions, the point of impact can be anywhere between 0-8 inches below the die tip. Preferably, the point of impact is in the range of 1-3 inches inches below the die tip.

Figure 2:
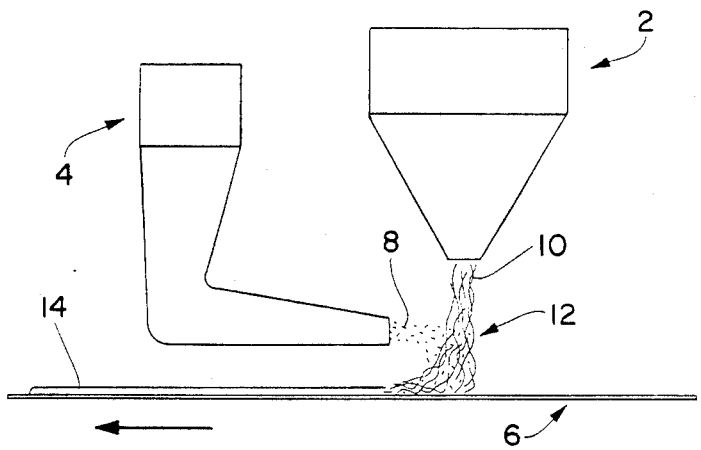
FIG. 2 is a side view of the apparatus shown in FIG. 1.

FIGS. 1 and 2 schematically show apparatus for forming the meltblown web of the present invention. Thus, conventional meltblowing die 2 is used to form the stream 10 of meltblown fibers of the polymer material. Particulate material 8 is fed, by the particle feed apparatus 4, into the stream 10 of meltblown fibers at the location indicated by reference numeral 12, to be incorporated among the meltblown fibers of the stream. Since the meltblown fibers are sufficientlyt acky at the point where the particles are incorporated into the stream, the particles adhere to the fibers upon contacting the fibers in the stream. The fibers, with the particles adhered thereto, are then collected on collecting surface 6 and formed into a web 14, using conventional consolidating techniques in melt-blowing. Since the particles were adhered to the surface of the fibers due to the tacky nature of the fibers at the point of incorporation of the particles into the stream of fibers, the particles are held within the web by such adherence. Thus, the particles are held within the web by more than mere physical entrapment of the particles among the fibers within the web, so that maintenance of the fibers in the web is improved (that is, the dusting problemis reduced).

As indicated previously, the present invention also contemplates incorporating the meltblown material as a layer of a laminate (e.g., a composite fabric), for example, as the intermediate layer of a composite laminate, with the outer two (sandwiching) layers providing mechanical strength and abrasion resistance to the laminate. As for the sandwiching layers that can be utilized, attention is directed to the previously discussed U.S. Pat. No. 4,433,024 to Eian; thus, nonwoven or woven fabrics, or even permeable films, can be used. As illustrative of this aspect of the present invention, a meltblown web can be laminated between two layers of 0.4 osy (ounces/yard$^2$) spunbond fabrics of, e.g., polypropylene. Lamination can be performed by conventional ultrasonic laminating techniques; ultrasonic bonding techniques are preferred for the laminating due to the heavy weight of the finished laminate (3.5-6.5 osy); however, other bonding techniques can be used. The area of the bonding was, e.g., 10% of the surface area of the web; such bonding area will retain maximum activity for the laminate (e.g., retain maximum absorbency for the particulate material in the meltblown web).

While the present aspect of the invention has been illustrated using spunbond fabric for the sandwiching layers (such spunbond fabric offers good abrasion resistance and is porous (breathable)), the present aspect of the invention is not limited thereto, and other porous sheet material can be used for the laminating layers.

As indicated previously, a further aspect of the present invention is the various applications of the meltblown material having particulate material distributed therein, and laminates including such particle-laden material. For example, the meltblown material can be used to provide both a filtering function and a deodorizing function; illustrative thereof, such meltblown web can include particulate material containing an odor-masking and/or deodorizing material. Webs including the odor masking and/or deodorizing particulate material are particularly useful for end uses where slightly to moderate odor problems occur, such as vacuum cleaner bags, especially disposable vacuum cleaning bags. For such end use, e.g. vacuum cleaner bags, the web can be incorporated in a fabric laminate of at least two layers, with at least one layer (the meltblown material) containing odor masking and/or deodorizing material (particulates) and at least one outer layer contributing strength and abrasion resistance. The outer layer can be, e.g., a porous spunbond layer, for forming a laminate improving strength properties of the web, as discussed previously. For use as a vacuum cleaner bag, such fabric laminate can be substituted for the material of the filtering bag of the vacuum cleaner, which filtering bag is shown, e.g., in FIG. 4 and the accompanying description in U.S. Pat. No. 4,257,791, the contents of which is incorporated herein by reference. Such filtering bag includes an opening for connection to the vacuum cleaner, whereby air and, e.g., dirt picked up by the vacuum cleaner passes into the bag, the air passing through the bag so as to separate the air and dirt.

The fabric can also be designed to contain particulate material to adsorb air-borne and vapor-borne odors, as well as to contain particulate material to slowly release a masking scent. The release of a masking scent can be achieved by using a superabsorber material that will slowly release an incorporated scent, similar to the mechanism by which superabsorbers slowly release moisture. As an example, time release fragrances, using a fragrance adsorbed on, e.g., a particulate silica surface, as known in the art, can be incorporated in the meltblown web. Other deodorants and masking scents, known in the art, which can be incorporated in particle form in the web, include the maladates, commonly known as chemical masking agents. The deodorants and/or masking scents can be incorporated in the meltblown web in amounts of, e.g., 0.50%-60% by weight of the web, to provide the desired function.

Another problem associated with vacuuming is dust leaking through the bag back into the atmosphere. Such problem can be avoided using the meltblown material of the present invention, since the natural filtration of such meltblown material itself will prevent much of this from occurring. In this regard, the porosity of the meltblown material can be controlled (e.g., by controlling the fiber diameter of the meltblown fibers) so as to provide effective filtering of the dust particles.

The application of the particle-laden meltblown material of the present invention to vacuum cleaner bags and the like has the following advantages:

(1) A cost-competitive product with added features of (a) eliminating odors; and (b) substantially eliminating vacuumed particles from re-entering the atmosphere; and (2) The product can be tailored to specific end uses by varying the additives (e.g., particulate additives).

Various examples of meltblowing and particle feeding processing conditions will be set forth as illustrative of the present invention. Of course, such examples are illustrative, and are not limiting. In connection with these processing conditions, FIGS. 1 and 2, and the previous discussion of the particle feeding and meltblowing techniques, are noted.

EXAMPLE 1

Meltblowing process conditions:
Polymer: Estane ® 58887 Polyurethane (B. F. Goodrich)
Melt Temperature 406° F.
Die Tip Pressure: 215 psig
Air Gap: 0.090 inch
Primary Air Temperature: 508° F. Oxy-dry ® powder feed conditions:
Particulate: Unisorb ® Mark II (from Contamination Control, Inc.). This material is constituted by potassium permanganate on an active alumina substrate. The particulate has a median particle size of 200µ, with a particle size range of 50-300µ.
Feed roll setting: 80% of maximum feed
The technique described above provided a 45% by weight loading of particulate in the finished material.

EXAMPLE 2

Meltblowing process conditions:
Polymer Blend: Kraton ®G 1657 (Shell)—60% (by weight); Polyethylene 601 (U.S.I.)—40% (by weight)
Melt Temperature: 540° F.
Die Tip Pressure: 174 psig
Air Gap: 0.090 inch
Primary Air Temperature: 578° F. Oxy-dry ® powder feed conditions:
Particulate: AX-21 Active Carbon (Anderson Devel. Co.). The particulate has a median particle size of 170µ, with a particle size range of 10-350µ.
Feed roll setting: 70% of maximum feed
The technique described above provides a 32% by weight loading of particulate in the finished material.

EXAMPLE 3

Meltblowing process conditions:
Polymer: Polypropylene PC-973 (Himont)
Melt Temperature: 519° F.
Die Tip Pressure: 82 psig
Air Gap: 0.067 inch
Primary Air Temperature: 572° F.
Oxy-dry ® powder feed conditions:
Particulate: Baking soda. The particulate has a particle size range of 100-350µ.
Feed roll setting: 80% of maximum feed
The technique described above provided a 45% by weight loading of particulate in the finished material.

By the various aspects of the present invention, the following advantages are achieved:

(1) Dusting is substantially eliminated, or at least minimized;

(2) No binders are used, thus eliminating the blocking of the active sites;

(3) An abrasion resistant fabric is produced;

(4) The process avoids the melt strength problem which causes severe difficulties in producing particle-laden nonwoven fabrics by phase separation spinning techniques;

(5) Higher particle loadings are possible than with phase separation spinning;

(6) Particle or compound preparation is essentially not required;

(7) No extraction of spinning solvent is needed, allowing a much less expensive product; and (8) Ultrasonic bonding can be utilized, allowing for a drapable/strong fabric while minimizing activity loss.

While we have shown and described several embodiments in accordance with the present invention, it is understood that the same is not limited thereto but is susceptible of numerous changes and modifications as known to one having ordinary skill in the art and we therefore do not wish to be limited to the details shown and described herein, but intend to cover all such modifications as are encompassed by the scope of the appended claims.

What is claimed is:

1. A substantially non-dusting nonwoven material comprising:
   a web of meltblown fibers having a diameter of from less than about 1 micron to about 25 microns, said fibers comprising a blend of a polyolefin and from about 5% to about 30%, by weight, of an adhesive polymer selected from the group consisting of polybutylene and polyethylene acrylic acid; and
   up to about 35%, by weight, based on the weight of the nonwoven material, of unblocked active particles, ranging in size from about 50 to about 150 microns, adhered to the surface of said fibers and distributed throughout said web.

2. The nonwoven material according to claim 1, wherein said adhesive polymer is selected from the group consisting of polybutylene and polyethylene acrylic acid.

3. The nonwoven material according to claim 2, wherein said fibers comprise polypropylene.

4. The nonwoven material according to claim 1, wherein said particles are selected from the group consisting of activated carbon, potassium permanganate, baking soda, clays, diatomaceous earth, and complexes of potassium permanganate with active alumina.

5. A substantially non-dusting laminate comprising:
   a nonwoven material including meltblown fibers having a diameter of from less than about 1 micron to about 25 microns, said fibers comprising a blend of a polyolefin and from about 5% to about 30%, by weight, of an adhesive polymer selected from the group consisting of polybutylene and polyethylene acrylic acid and up to about 35%, by weight, based on the weight of the laminate, of unblocked active particles, ranging in size from about 50 to about 150 microns, adhered to the surface of said fibers and distributed through said nonwoven material; and
   at least one reinforcing layer of a material that provides increased abrasion resistance and mechanical strength to the laminate as compared to the abrasion resistance and mechanical strength of the nonwoven material.

6. The laminate according to claim 5, comprising at least two reinforcing layers which sandwich said nonwoven material.

7. The laminate according to claim 5, wherein said reinforcing layer comprises a spunbonded sheet material.

8. The laminate according to claim 5, wherein the reinforcing layer is bonded to the nonwoven material by ultrasonic bonding.

9. The laminate according to claim 8, wherein 10% of the area of the laminate is bonded.

10. A nonwoven material comprising:
    a web of meltblown fibers comprising a blend of polypropylene and from about 5% to about 30%, by weight, of an adhesive polymer selected from the group consisting of polybutylene and polyethylene acrylic acid; and
    up to about 60%, by weight, based on the weight of the nonwoven material, of unblocked active particles, ranging in size from about 50 to about 150 microns, adhered to the surface of said fibers and distributed throughout said web.

11. The nonwoven material according to claim 10, wherein said meltblown fibers have a diameter of from less than about 1 micron to about 25 microns.

12. The nonwoven material according to claim 10, wherein said particles are selected from the group consisting of activated carbon, potassium permanganate and baking soda.

13. A laminate comprising:
    a nonwoven material including meltblown fibers having a diameter of from less than about 1 micron to about 25 microns, said fibers comprising a blend of a polyolefin and from about 5% to about 30%, by weight, of an adhesive polymer selected from the group consisting of polybutylene and polyethylene acrylic acid and up to about 60%, by weight, based on the weight of the laminate, of unblocked active particles, ranging in size from about 50 to about 150 microns, adhered to the surface of said fibers and distributed through said nonwoven material; and
    at least one reinforcing layer of a material that provides increased abrasion resistance and mechanical strength to the laminate as compared to the abrasion resistance and mechanical strength of the nonwoven material;
    wherein about 10% of said reinforcing layer is bonded to said composite web.

* * * * *

UNITED STATES PATENT AND TRADEMARK OFFICE
CERTIFICATE OF CORRECTION

PATENT NO. : 4,797,318
DATED : January 10, 1989
INVENTOR(S) : Ronald W. Brooker, et al.

It is certified that error appears in the above—identified patent and that said Letters Patent is hereby corrected as shown below:

Column 1, lines 3 and 4 "Uses Thereof" should read --Uses Therefor--.

Column 3, line 3 "for the air", should read --from the air--.

Column 5, line 39 "particule", should read --particle--.

Column 6, line 28 "inches inches", should read --inches--.

Column 6, line 39 "sufficientlyt acky", should read --sufficiently tacky--.

Column 6, line 52 "problems", should read --problem is--.

Column 7, line 24 "slightly" should read --slight--.

Signed and Sealed this

Twenty-eighth Day of April, 1992

*Attest:*

HARRY F. MANBECK, JR.

*Attesting Officer*  *Commissioner of Patents and Trademarks*